(12) United States Patent
Chang

(10) Patent No.: US 8,034,025 B1
(45) Date of Patent: Oct. 11, 2011

(54) DISPOSABLE SAFETY SYRINGE

(76) Inventor: Shu-Ming Chang, Nantou (TW)

( * ) Notice: Subject to any disclaimer, the term of this patent is extended or adjusted under 35 U.S.C. 154(b) by 0 days.

(21) Appl. No.: 12/821,137

(22) Filed: Jun. 23, 2010

(51) Int. Cl.
*A61M 5/00* (2006.01)
*A61M 5/31* (2006.01)

(52) U.S. Cl. ........ 604/110; 604/187; 604/218; 604/228; 604/241; 604/243

(58) Field of Classification Search ................. None
See application file for complete search history.

(56) References Cited

U.S. PATENT DOCUMENTS 5,533,970 A * 7/1996 Berger et al. ................. 604/110
6,706,015 B2 * 3/2004 Bang ............................ 604/110
2005/0096602 A1 * 5/2005 Lin .............................. 604/221

* cited by examiner

*Primary Examiner* — Nicholas D Lucchesi
*Assistant Examiner* — Leah Stohr

(57) ABSTRACT

A disposable safety syringe in one embodiment includes a syringe barrel; a plunger comprising a push rod; hollow first, second, and third adapters for forming an airtight engagement with an inner surface at one end of the syringe barrel; and a needle threadedly secured to the first adapter to establish a communication with inside of the syringe barrel prior to beginning a liquid dispensing operation with respect to a subject. After injection and pulling the needle out of a subject, a pulling of the plunger can be stopped, a further pulling of the plunger can also be stopped when an annular cutting groove of the plunger is about flush with the other end of the syringe barrel with the needle being retracted into the syringe barrel, and a breaking operation along the cutting groove can break the plunger.

6 Claims, 8 Drawing Sheets

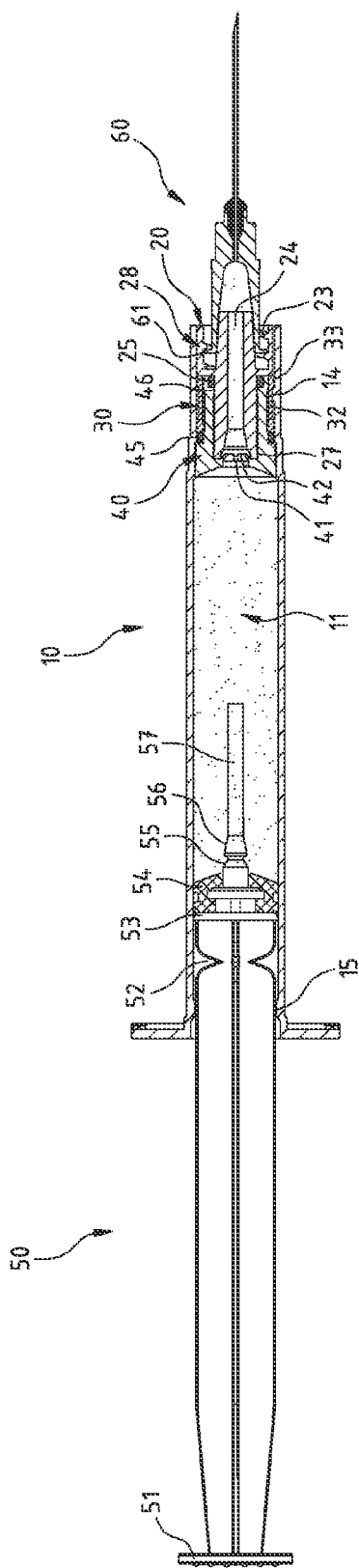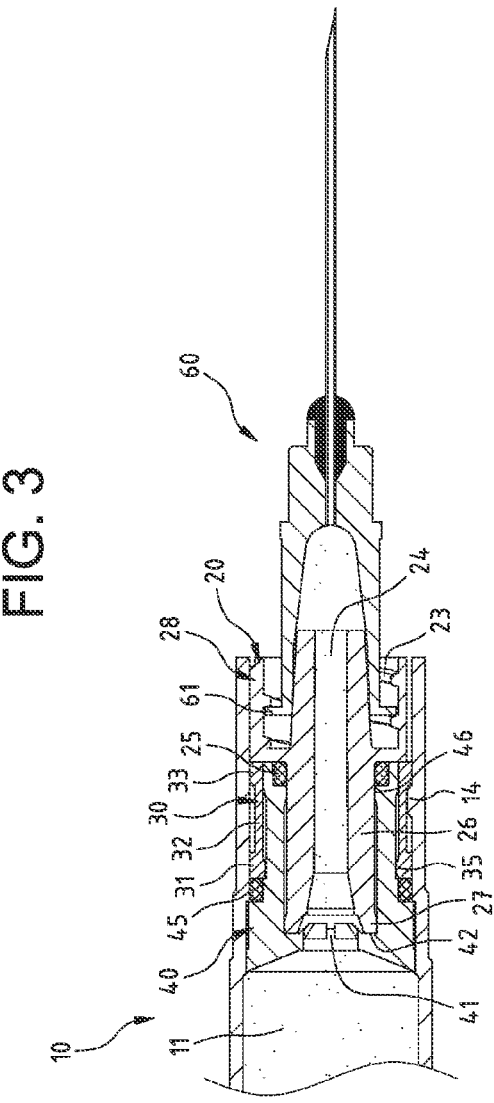

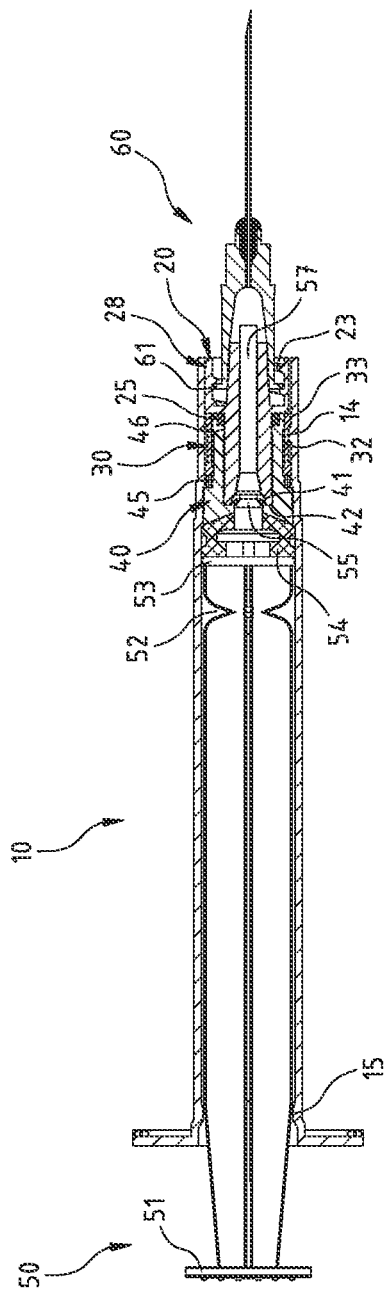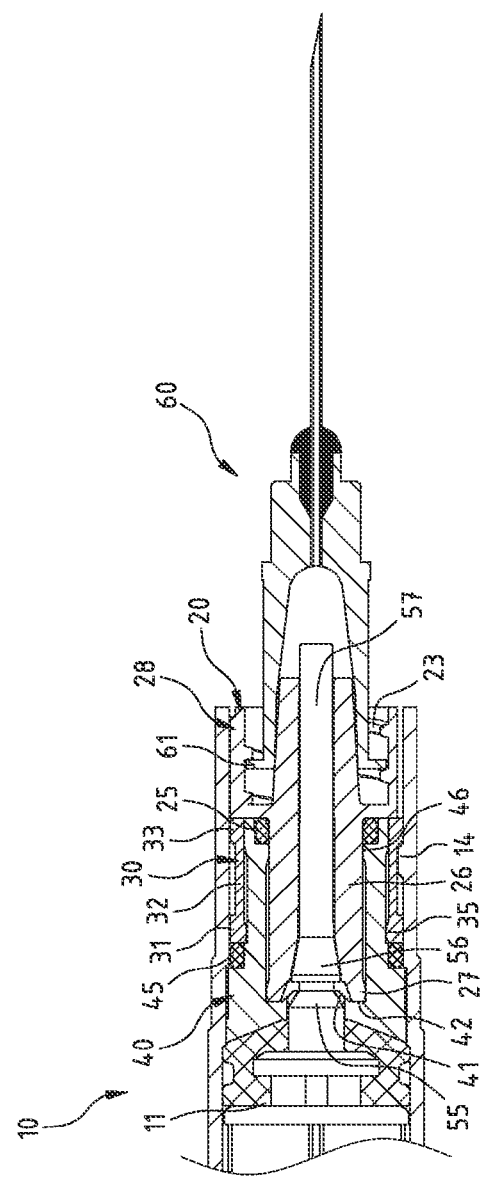

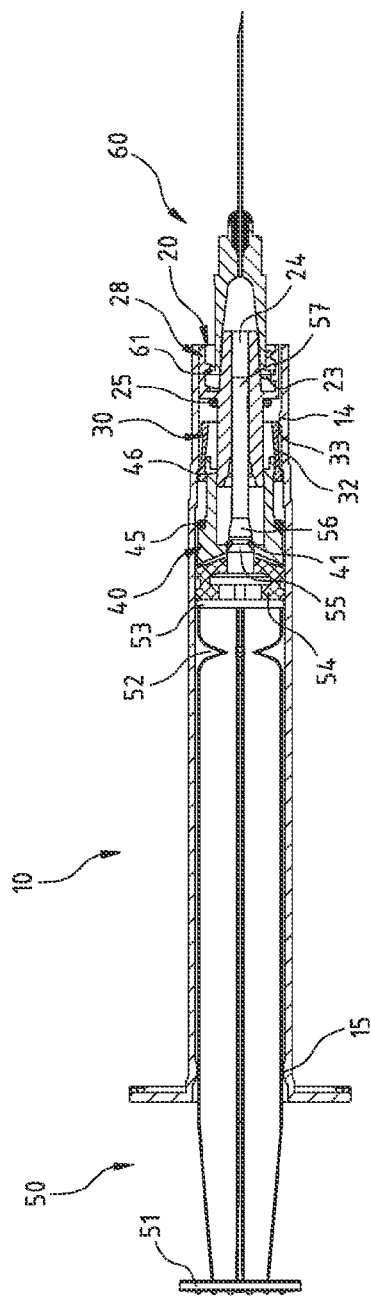
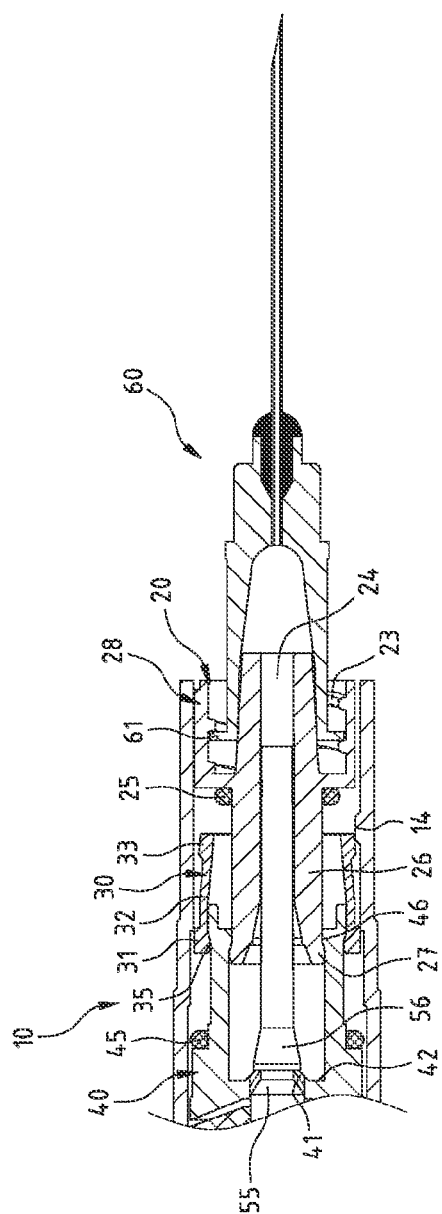
FIG. 9
FIG. 10

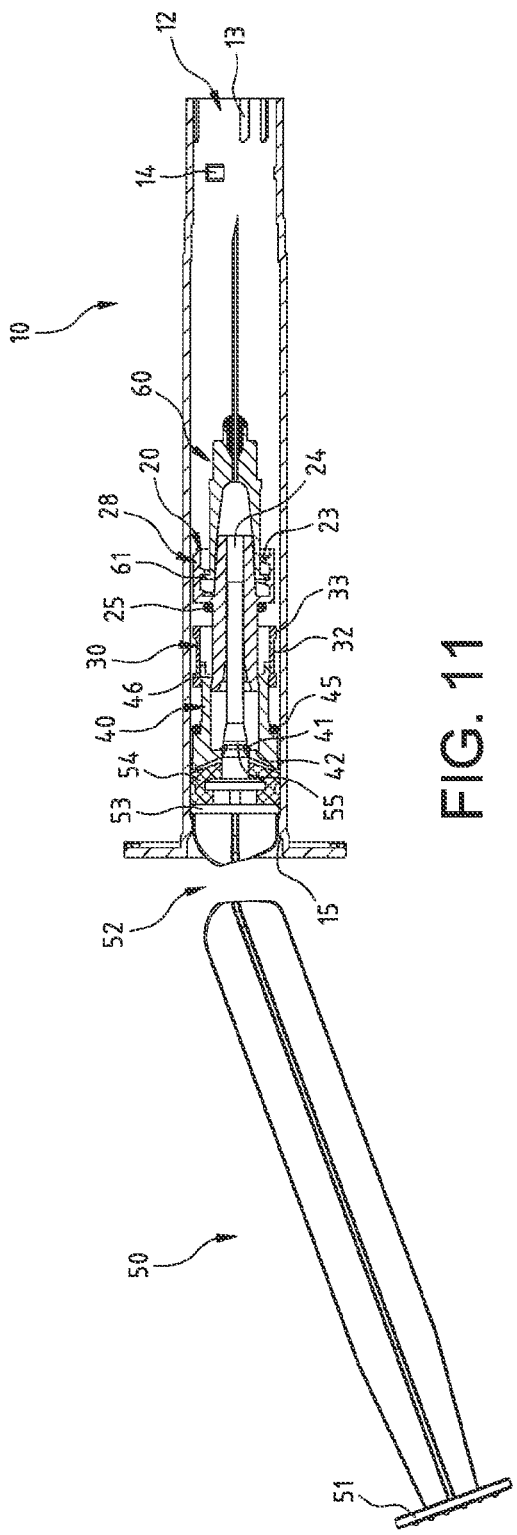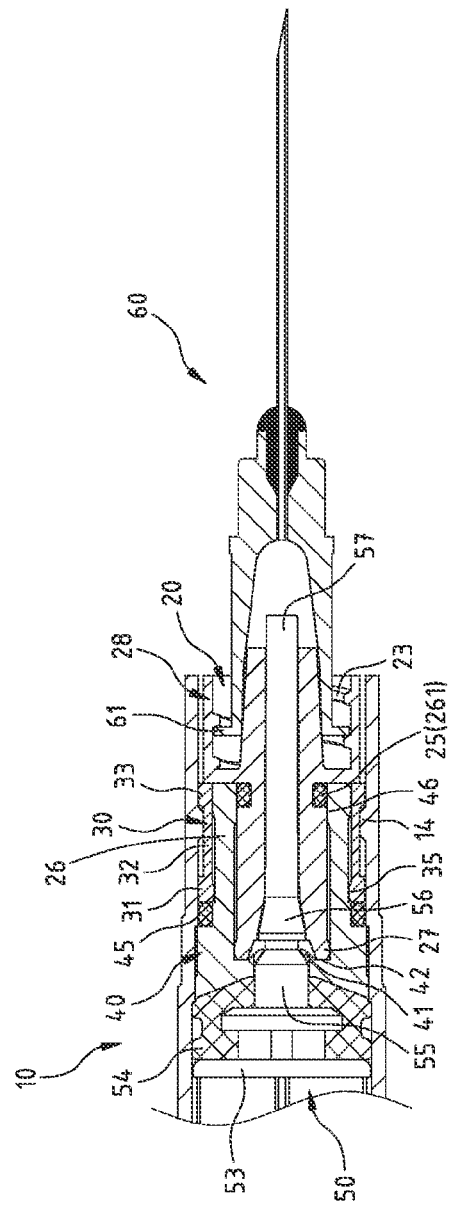

DISPOSABLE SAFETY SYRINGE

BACKGROUND OF THE INVENTION

1. Field of Invention

The invention relates to medical instruments and more particularly to a safety syringe which, after a single use, can be discarded for preventing contamination by retracting the needle into the syringe barrel and breaking the plunger.

2. Description of Related Art

Safety syringes are medical instruments for dispensing liquid preparations or withdrawing liquid medicines. However, medical employees such as doctors and nurses are liable to accidental puncture of the skin by a needle. The problem can be serious if the needle has been used. Recently, diseases (some fatal), such as hepatitis and Acquired Immune Deficiency Syndrome (AIDS), can be contracted if the needle has been used on an infected person. For preventing contamination, safety syringes are developed and commercially available.

A conventional disposable safety syringe comprises a barrel, a plunger inserted into the barrel, a needle hub provided at a front end of the barrel to hold a needle, and a block member having a through hole provided in the needle hub. The barrel has an annular groove on a front wall around the needle hub. After engaging the head of the plunger with the needle hub, the plunger can be pulled backward to break the groove so that the needle hub and the needle are retracted into the barrel.

However, in the conventional safety syringe the thin groove on the front wall of the barrel may be broken during injection or transportation of the safety syringe due to thermal expansion and contraction of PP (polypropylene) material of the safety syringe, thereby causing a leakage of the fluid medicine. Further, the desired retraction of the needle hub into the barrel can be jammed due to temperature variations. Thus, the need for improvement still exists.

SUMMARY OF THE INVENTION

It is therefore one object of the invention to provide a safety syringe which, after a single use, can be discarded for preventing contamination by retracting a needle into a syringe barrel and breaking a plunger.

To achieve the above and other objects, the invention provides a disposable safety syringe comprising a syringe barrel having both ends open and comprising a plurality of projections equally spaced on an inner surface proximate one end, a plurality of axial raised limit members at one end, and an annular lip distal the limit members; a plunger comprising a push rod projecting out of one end, first locking means at a portion of the push rod joining one end of the plunger, a cylindrical sealing member at one end of the plunger, a stop ring abutted the sealing member, a cross shaped cutting groove adjacent the stop ring, and a thumb pad distal the sealing member; a hollow first adapter comprising a hollow, cylindrical body having locking means, a hollow cylinder extending through the body and being concentric therewith, a shoulder formed between the cylinder and the body, a plurality of risers on an outer surface of the body, a plurality of recesses each defined by the riser and the body, and a first O-ring abutted the shoulder; a tubular second adapter comprising a plurality of latches each having a raised curved member at one end, an annular flange at the other end, and an inward extending rim at the other end; a tubular third adapter having a stepped-diameter outer surface and comprising an enlargement at one end, a stepped-diameter section at one end, second locking means at the other end, and a second O-ring put on the outer surface of the third adapter; and a needle; wherein in an assembled state, wherein in an assembled state, the first adapter is inserted through the syringe barrel until the first adapter is disposed at one end, the first adapter is turned to align the recesses with the limit members, the first adapter is pushed to lockingly dispose the limit members in the recesses, the second adapter is inserted through the syringe barrel to put on the cylinder with the latches being lockingly urged against the projections, the third adapter is inserted through the syringe barrel into a cylindrical space between the cylinder and the second adapter until the first O-ring is clamped by the stepped-diameter section so as to form an airtight engagement of the first, second, and third adapters at one end with the first, second, and third adapters being secured together, and the needle is releasably secured to the locking member; wherein the needle establishes a communication with an internal space of the syringe barrel via the cylinder and the second locking means prior to beginning a liquid dispensing operation with respect to a subject; and wherein at end of the liquid injection operation, the push rod projects out of the cylinder into the needle, the first locking means and the second locking means are locked each other to fasten the plunger and the third adapter together, after a subsequent removing the needle out of the subject, a pulling of the plunger can be stopped when the enlargement is stopped by the rim and the stepped-diameter section is lockingly engaged with the rear end, a further pulling of the plunger can be stopped when the cutting groove is about flush with the other end of the syringe barrel with the needle being retracted into the syringe barrel, and a breaking operation along the cutting groove can break the plunger.

The above and other objects, features and advantages of the invention will become apparent from the following detailed description taken with the accompanying drawings.

BRIEF DESCRIPTION OF THE DRAWINGS

FIG. 3 is a longitudinal sectional view of the assembled safety syringe in FIG. 1 in which the syringe barrel is filled with liquid preparations to be dispensed;

FIG. 4 is a fragmentary view of the needle and adjacent parts in FIG. 3;

FIG. 5 is a view similar to FIG. 3 in which the liquid preparations have been dispensed;

FIG. 6 is a fragmentary view of the needle and adjacent parts in FIG. 5;

FIG. 9 is a view similar to FIG. 7 showing a second step of retracting the needle and adjacent parts into the syringe barrel after dispensing;

FIG. 10 is a fragmentary view of the needle and adjacent parts in FIG. 9;

FIG. 11 is a view similar to FIG. 9 showing the needle and adjacent parts have been retracted into the syringe barrel and the plunger has been broken in the final step of retracting the needle and adjacent parts into the syringe barrel after use;

FIG. 12 is a fragmentary view of a needle and adjacent parts according to a second preferred embodiment of disposable safety syringe of the invention;

DETAILED DESCRIPTION OF THE INVENTION

Referring to FIGS. 1 to 11, a disposable safety syringe in accordance with a first preferred embodiment of the invention comprises the following components as discussed in detail below.

Figure 1:
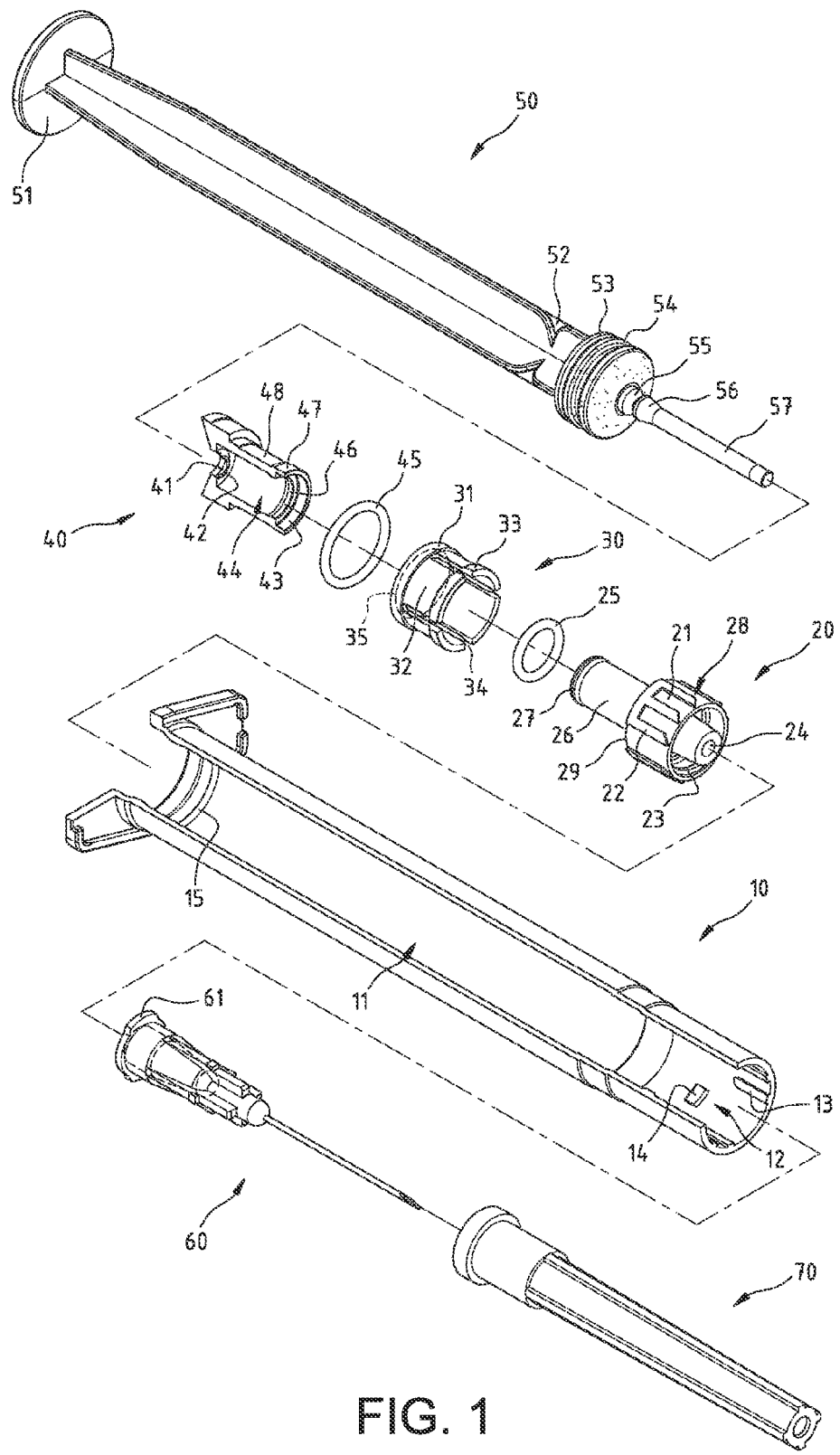
FIG. 1 is an exploded of a disposable safety syringe according to a first preferred embodiment of the invention.
Figure 2:
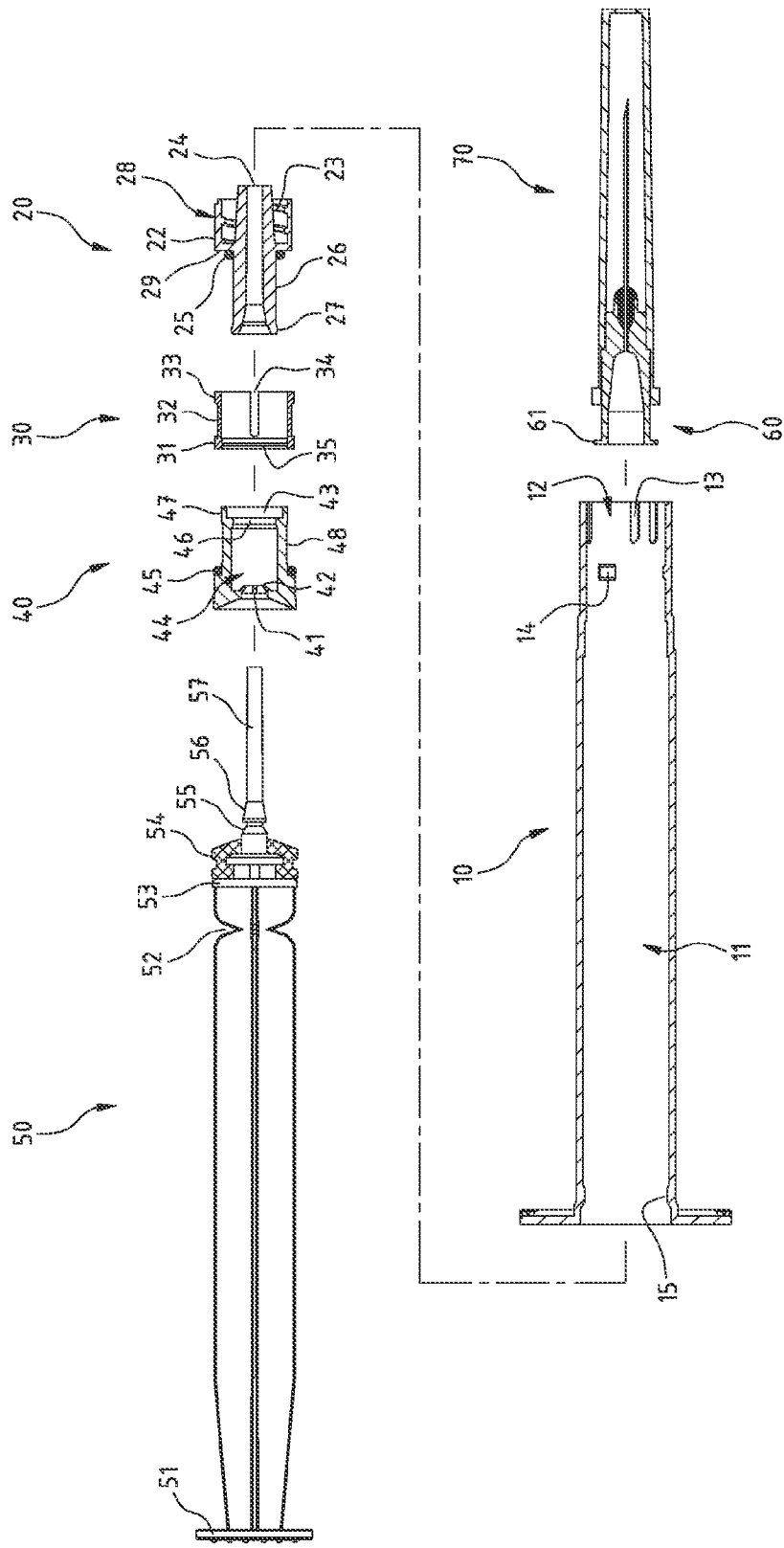
FIG. 2 is a longitudinal sectional view of the safety syringe in FIG. 1.
Figure 7:
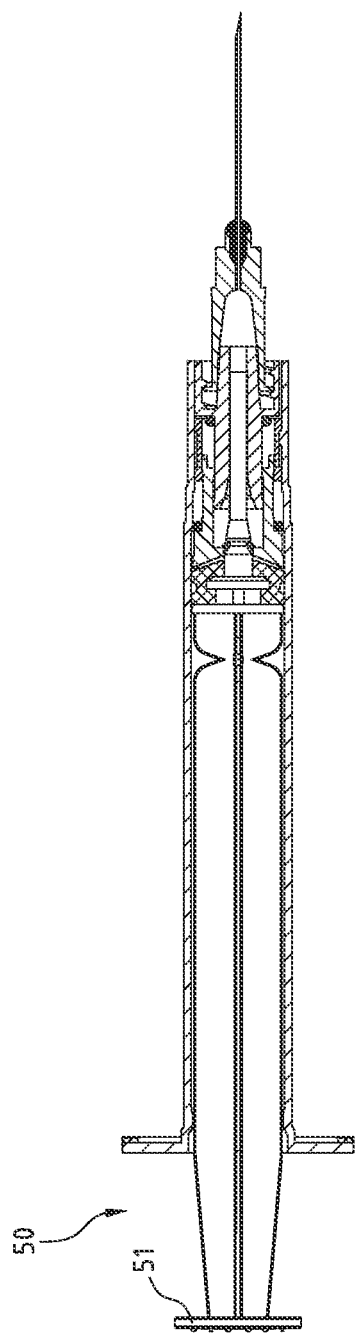
FIG. 7 is a view similar to FIG. 5 showing a first step of retracting the needle and adjacent parts into the syringe barrel after dispensing.
Figure 8:
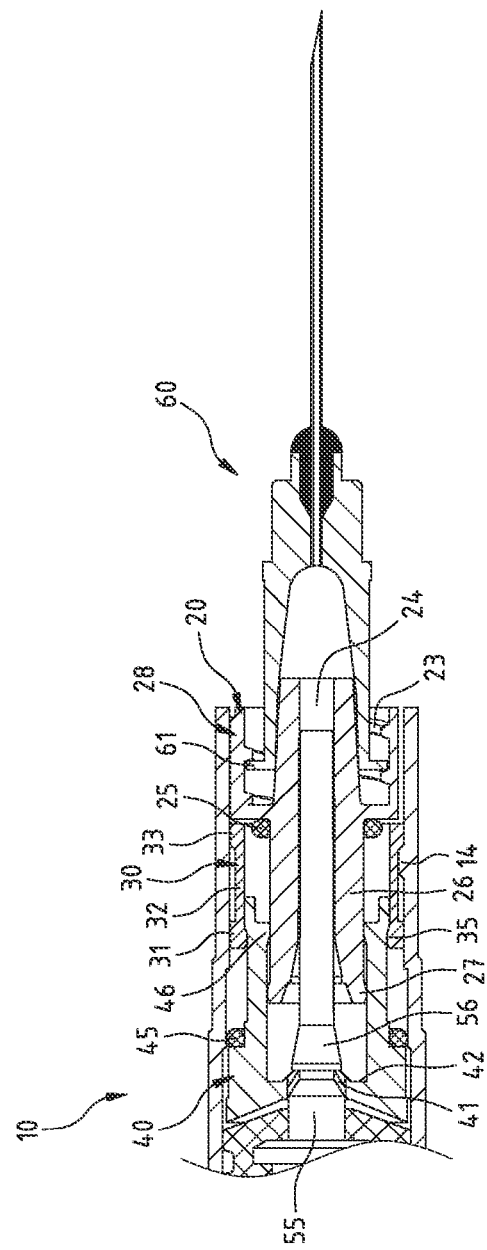
FIG. 8 is a fragmentary view of the needle and adjacent parts in FIG. 7.

A syringe barrel 10 comprises an internal space 11 for containing a quantity of liquid preparations, three spaced projections (only one is shown in FIG. 1) 14 equally spaced on an inner surface proximate one end 12, a plurality of axial raised limit members 13 at one end 12, and an annular lip 15 at the other end.

A plunger 50 comprises a push rod 57 projecting out of one end, a frusto-conical locking member 56 proximate the other end of the push rod 57, an annular groove 55 at the other end of the push rod 57 adjacent to the locking member 56, a cylindrical rubber sealing member 54 at one end of the plunger 50, an annular stop ring 53 proximate the sealing member 54, a cross shaped cutting groove 52 adjacent the stop ring 53, and a disc shaped thumb pad 51 at the other end. The portion of the plunger 50 between the stop ring 53 and the thumb pad 51 has a cross-section of cross. A needle 60 has a toothed rear hub 61.

An airtight adapter assembly is provided at one end 12 of the syringe barrel 10 and comprises first, second and third adapters 20, 30 and 40. The hollow first adapter 20 comprises a hollow forward cylindrical body 28, threads 23 on an inner surface of the body 28 to be threadedly (i.e., releasably) secure to the toothed hub 61, a hollow rear cylinder 26 having a diameter less than that of the body 28 and having a tunnel 24 projecting through the body 28 (i.e., concentric) and further out of the mouth of the body 28 a small distance, the cylinder 26 having a flared rear end 27, a shoulder 29 between the large body 28 and the small cylinder 26, three spaced risers 22 on an outer surface of the body 28, a plurality of recesses 21 each defined by either half of the riser 22, and an O-ring 25.

The tubular third adapter 40 comprises an axial channel 44, a locking element 41 at the other end, an annular bottom wall 42 proximate the locking element 41, an enlargement 47 at one end, an annular wall 43 open to one end, an annular shoulder 46 adjacent the wall 43, a smooth intermediate portion 48, and an O-ring 45.

The tubular second adapter 30 comprises a raised other end 31, four latches 32 equally spaced around the other end 31, each latch 32 having a raised curved end 33, an inward extending rim 35 on an inner surface of the other end 31, and a space 34 defined by any two adjacent latches 32.

A partial assembly of the safety syringe will be described in detail below. The O-ring 45 is put on a shoulder behind the intermediate portion 48. The O-ring 25 is put on the joining portion of the shoulder 29 and the cylinder 26. Next, the first adapter 20 is inserted through the other end of the syringe barrel 10 through the projections 14 (i.e., each projection 14 passing the gap between any two adjacent risers 22) until the first adapter 20 reaches one end 12 with the recesses 21 aligned with the limit members 13. Next, further push the first adapter 20 to complementarily dispose the limit members 13 in the recesses 21 for locking (i.e., a turning of the first adapter 20 with respect to the syringe barrel 10 and a forward pushing of the first adapter 20 are prohibited). Next, the second adapter 30 is put on the cylinder 26 by inserting through the other end of the syringe barrel 10 with the projections 14 passing the raised curved ends 33 to fasten in the spaces 34. That is, each projection 14 is secured to the latch 32. Next, the third adapter 40 is inserted through the other end of the syringe barrel 10 into a cylindrical gap between the cylinder 26 and the second adapter 30 until the O-ring 25 is fitted in the annular wall 43 and the O-ring 45 is biased between the shoulder behind the intermediate portion 48 and the raised other end 31. The shoulder 29 acts as a stop member by tightly engaging with the front ends of both the second and third adapters 30, 40. The latches 32 thus press the enlargement 47 and the shoulder 46 to clamp the cylinder 26. Hence, a rearward removal of the adapter assembly from the syringe barrel 10 is prohibited. Next, insert the plunger 50 into the syringe barrel 10 until the push rod 57 is disposed in the tunnel 24 but the locking member 56 is not engaged with the locking element 41. Next, a protective cap 70 is put on a cylindrical portion of the hub 61 to hide the elongated needle 60 and frictionally fastened together. Next, the needle 60 is attached to and secured to the first adapter 20 by rotating the hub 61 along the spiral groove of the threads 23 in a storage position of the syringe.

A liquid dispensing operation of the syringe will be discussed in detailed below. First, remove the cap 70 from the needle 60. Next, pull the plunger 50 to create vacuum in the syringe barrel 10. Next, push the plunger 50 until the push rod 57 projects out of the tunnel 24 into a rear chamber of the needle 60 but the locking member 56 is still not engaged with the locking element 41 (i.e., spaced from the locking element 41 by a small distance). Next, insert the needle 60 into an injection liquid container (not shown). Next, pull the plunger 50 backward to withdraw a desired amount of liquid preparations from the container into the airtight, leak free space 11 via the needle orifice, the tunnel 24, the bottom wall 42, and the locking element 41 due to the substantially vacuum state of the syringe barrel 10. Next, remove the needle 60 from the container. Next, replace the needle 60 with another needle 60 having a smaller orifice (optional). Next, slowly push the plunger 50 to expel remaining air in the front portion of the space 11 and a minimum amount of liquid preparations out of the orifice of the needle 60. Next, insert the needle 60 into the skin of a patient and slowly push the plunger 50 to completely inject the liquid preparations into the patient. At end of the injection, the locking member 56 and the groove 55 together are matingly lockingly engaged with the locking element 41 and the bottom wall 42 (see FIG. 6). That is, the plunger 50 and the third adapter 40 can move as a whole.

Next, remove the needle 60 from the patient. Next, pull both the plunger 50 and thus the third adapter 40 backward until the enlargement 47 is stopped by the rim 35 (see FIG. 8). Next, further pull the plunger 50 to disengage the projections 14 from the latches 32. Next, further pull the plunger 50 until the shoulder 46 is stopped by the rear end 27 and secured together. Hence, the plunger 50, the third adapter 40, the second adapter 30, and the first adapter 20 can move as a whole. Next, further pull the plunger 50, the third adapter 40, the second adapter 30, and the first adapter 20 backward until they completely disengage from one end 12 and the stop ring 53 is engaged with and stopped by the lip 15. At this position, the cutting groove 52 is about flush with the other end of the syringe barrel 10 and the adapter assembly and the needle 60 are completely retracted into the syringe barrel 10 (see FIG. 11). Thereafter, a medical employee doing the dispensing operation can break the plunger 50 along the cutting groove 52. Finally, two broken parts of the syringe can be discarded to finish a safe disposal. This can prevent a next use of the syringe from occurring since it may be contaminated in the above dispensing operation.

Referring to FIG. 12, a disposable safety syringe in accordance with a second preferred embodiment of the invention is characterized below. An annular trough 261 is formed around the cylinder 26 at a joining portion of the shoulder 29 and the cylinder 26. The O-ring 25 can be fitted in the trough 261. Also, an inner surface of the front end portion of the third adapter 40 is a smooth even surface and is tightly clamped around the O-ring 25. Further, the number of the projections 14 is a multiple of two and the projections 14 are symmetrical.

Figure 13:
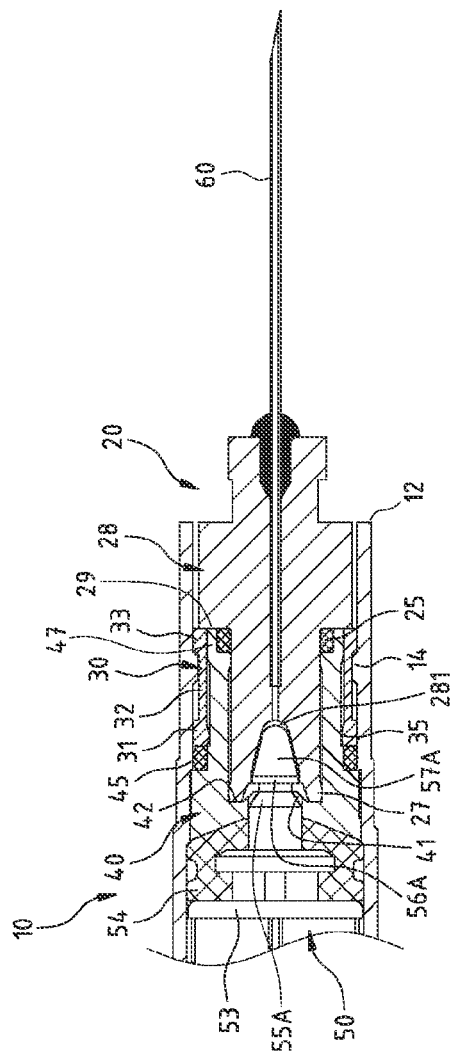
FIG. 13 is a fragmentary view of a needle and adjacent parts according to a third preferred embodiment of disposable safety syringe of the invention.

Referring to FIG. 13, a disposable safety syringe in accordance with a third preferred embodiment of the invention is characterized below. The body 28 of the first adapter 20 is formed integrally with the needle 60. A substantially conic chamber 281 is formed on a rear end of the body 28. The push member 57A is shaped as a bullet head and is complementarily disposed in the chamber 281. The locking member 56A and the groove 55A together are matingly lockingly engaged with the locking element 41 and the bottom wall 42. Further, the number of the projections 14 is a multiple of two and the projections 14 are symmetrical.

Figure 14:
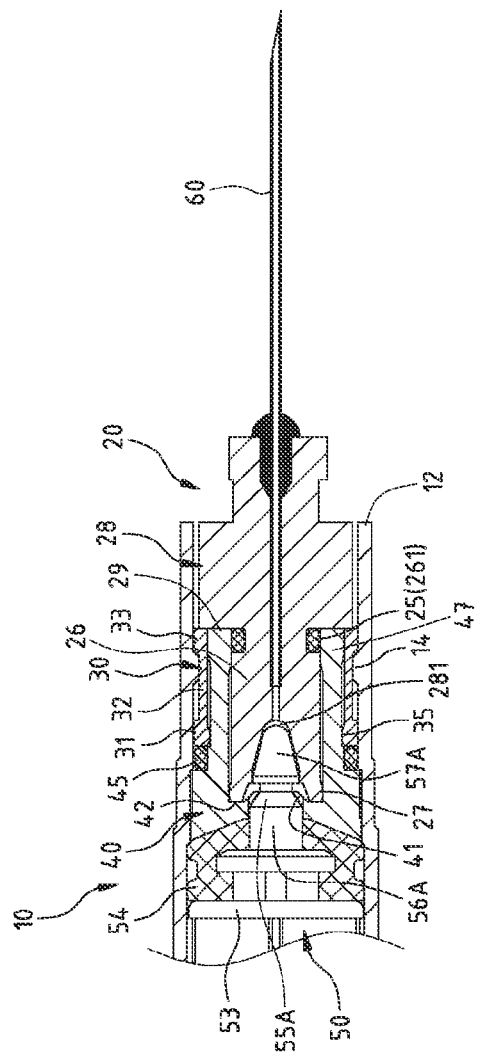
FIG. 14 is a fragmentary view of a needle and adjacent parts according to a fourth preferred embodiment of disposable safety syringe of the invention.

Referring to FIG. 14, a disposable safety syringe in accordance with a fourth preferred embodiment of the invention is characterized below. The fourth preferred embodiment is a combination of the second and third preferred embodiments. In detail, an annular trough 261 is formed around a reduced diameter cylinder 26 abutted the shoulder 29. The O-ring 25 can be fitted in the trough 261. Also, an inner surface of the front end portion of the third adapter 40 is a smooth even surface and is tightly clamped around the O-ring 25. The cylindrical body 28 of the first adapter 20 is formed integrally with the needle 60. A substantially conic chamber 281 is formed on a rear end of the body 28. The push member 57A is shaped as a bullet head and is complementarily disposed in the chamber 281. The locking member 56A and the groove 55A together are matingly lockingly engaged with the locking element 41 and the bottom wall 42. Furthermore, the projections 14 are equally spaced apart.

While the invention has been described in terms of preferred embodiments, those skilled in the art will recognize that the invention can be practiced with modifications within the spirit and scope of the appended claims.

What is claimed is:

1. A disposable safety syringe comprising:
    a syringe barrel (10) having both ends open and comprising a plurality of projections (14) equally spaced on an inner surface proximate one end (12), a plurality of axial raised limit members (13) at one end (12), and an annular lip (15) distal the limit members (13);
    a plunger (50) comprising a push rod (57) projecting out of one end, first locking means (55, 56) at a portion of the push rod (57) joining one end of the plunger (50), a cylindrical sealing member (54) at one end of the plunger (50), a stop ring (53) abutted the sealing member (54), a cross shaped cutting groove (52) adjacent the stop ring (53), and a thumb pad (51) distal the sealing member (54);
    a hollow first adapter (20) comprising a hollow, cylindrical body (28) having a locking member (23), a hollow cylinder (26) extending through the body (28) and being concentric therewith, the cylinder (26) having a flared rear end (27), a shoulder (29) formed between the cylinder (26) and the body (28), a plurality of risers (22) on an outer surface of the body (28), a plurality of recesses (21) each defined by the riser (22) and the body (28), and a first O-ring (25) abutted the shoulder (29);
    a tubular second adapter (30) comprising a plurality of latches (32) each having a raised curved member (33) at one end, an annular flange (31) at the other end, and an inward extending rim (35) at the other end;
    a tubular third adapter (40) having a stepped-diameter outer surface and comprising an enlargement (47) having annular inner wall (43) at one end, a stepped-diameter section (46) adjacent the inner wall (43), second locking means (41, 42) at the other end, and a second O-ring (45) put on the outer surface of the third adapter (40);
    wherein in an assembled state, the first adapter (20) is inserted through the syringe barrel (10) until the first adapter (20) is disposed at one end (12) with the recesses (21) aligned with the limit members (13), the first adapter (20) is pushed to lockingly dispose the limit members (13) in the recesses (21), the second adapter (30) is inserted through the syringe barrel (10) to put on the cylinder (26) with the latches (32) being lockingly urged against the projections (14), the third adapter (40) is inserted through the syringe barrel (10) into a cylindrical space between the cylinder (26) and the second adapter (30) until the first O-ring (25) is clamped by the inner wall (43) so as to form an airtight engagement of the first, second, and third adapters (20, 30, 40) at one end (12) with the first, second, and third adapters (20, 30, 40) being secured together.

2. The disposable safety syringe of claim 1, wherein the number of the projections (14) is at least two.

3. A disposable safety syringe comprising:
    a syringe barrel (10) having both ends open and comprising a plurality of projections (14) equally spaced on an inner surface proximate one end (12), and an annular lip (15) distal the projections (14);
    a plunger (50) comprising a substantially conic push member (57A) projecting out of one end, first locking means (55A, 56A) at a portion of the push member (57A) joining one end of the plunger (50), a cylindrical sealing member (54) at one end of the plunger (50), a stop ring (53) abutted the sealing member (54), a cross shaped cutting groove (52) adjacent the stop ring (53), and a thumb pad (51) distal the sealing member (54);
    a hollow first adapter (20) comprising a stepped-diameter cylindrical body (28) having an intermediate annular shoulder (29), a needle (60) integrally formed with the body (28), a first O-ring (25) abutted the shoulder (29), and a chamber (281) opposing the first O-ring (25) and the needle (60);
    a tubular second adapter (30) comprising a plurality of latches (32) each having a raised curved member (33) at one end, an annular flange (31) at the other end, and an inward extending rim (35) at the other end;
    a tubular third adapter (40) having a stepped-diameter outer surface and comprising an enlargement (47) at one end, second locking means (41, 42) at the other end, and a second O-ring (45) put on the outer surface of the third adapter (40);
    wherein in an assembled state, the first adapter (20) and the needle (60) together are inserted through the syringe barrel (10) until the first adapter (20) is disposed at one end (12), the first adapter (20) is turned to align the recesses (21) with the limit members (13), the first adapter (20) is pushed to lockingly dispose the limit members (13) in the recesses (21), the second adapter (30) is inserted through the syringe barrel (10) to put on the cylinder (26) with the latches (32) being lockingly urged against the projections (14) by urging, and the third adapter (40) is inserted through the syringe barrel (10) into a cylindrical space between the cylinder (26) and the second adapter (30) until the first O-ring (25) is clamped by the stepped-diameter section (46) so as to form an airtight engagement of the first, second, and third adapters (20, 30, 40) at one end (12) with the first, second, and third adapters (20, 30, 40) being secured together;

wherein the needle (60) establishes a communication with interior of the syringe barrel (10) via the chamber (281) and the second locking means (41, 42) prior to beginning a liquid dispensing operation with respect to a subject; and wherein at end of the liquid injection operation, the push member (57A) is disposed in the chamber (281), the first locking means (55A, 56A) and the second locking means (41,42) are locked each other to fasten the plunger (50) and the third adapter (40) together, after a subsequent removing the needle (60) out of the subject, a pulling of the plunger (50) can be stopped when the enlargement (47) is stopped by the rim (35), a further pulling of the plunger (50) can be stopped when the cutting groove (52) is about flush with the other end of the syringe barrel (10) with the needle (60) being retracted into the syringe barrel (10), and a breaking operation along the cutting groove (52) can break the plunger (50).

4. The disposable safety syringe of claim 3, wherein the number of the projections (14) is at least two.

5. A disposable safety syringe comprising:

a syringe barrel (10) having both ends open and comprising a plurality of projections (14) equally spaced on an inner surface proximate one end (12), and an annular lip (15) distal the projections (14);

a plunger (50) comprising a substantially conic push member (57A) projecting out of one end, first locking means (55A, 56A) at a portion of the push member (57A) joining one end of the plunger (50), a cylindrical sealing member (54) at one end of the plunger (50), a stop ring (53) abutting the sealing member (54), a cross shaped cutting groove (52) adjacent the stop ring (53), and a thumb pad (51) distal the sealing member (54);

a hollow first adapter (20) comprising a stepped-diameter cylindrical body (28) having a reduced diameter section (26), an annular shoulder (29) between the body (28) and the reduced diameter section (26), an annular trough (261) on the reduced diameter section (26) abutted the shoulder (29), a needle (60) integrally formed with the body (28), a first O-ring (25) disposed in the trough (261), and a chamber (281) distal the first O-ring (25) and the needle (60);

a tubular second adapter (30) comprising a plurality of latches (32) each having a raised curved member (33) at one end, an annular flange (31) at the other end, and an inward extending rim (35) at the other end; and a tubular third adapter (40) having a stepped-diameter outer surface and comprising an enlargement (47) at one end, second locking means (41, 42) at the other end, and a second O-ring (45) put on the outer surface of the third adapter (40);

wherein in an assembled state, the first adapter (20) and the needle (60) together are inserted through the syringe barrel (10) until the first adapter (20) is disposed at one end (12), the first adapter (20) is turned to align the recesses (21) with the limit members (13), the first adapter (20) is pushed to lockingly dispose the limit members (13) in the recesses (21), the second adapter (30) is inserted through the syringe barrel (10) to put on the cylinder (26) with the latches (32) being lockingly urged 5 against the projections (14) by urging, and the third adapter (40) is inserted through the syringe barrel (10) into a cylindrical space between the cylinder (26) and the second adapter (30) until the first O-ring (25) is clamped by the stepped-diameter section (46) so as to form an airtight engagement of the first, second, and third adapters (20, 30, 40) at one end (12) with the first, second, and third adapters (20, 30, 10 40) being secured together;

wherein the needle (60) establishes a communication with interior of the syringe barrel (10) via the chamber (281) and the second locking means (41, 42) prior to beginning a liquid dispensing operation with respect to a subject; and wherein at end of the liquid injection operation, the push member (57A) is disposed in the chamber (281), the first locking means (55A, 56A) and the second locking means (41,42) are locked each other to fasten the plunger (50) and the third adapter (40) together, after a subsequent removing the needle (60) out of the subject, a pulling of the plunger (50) can be stopped when the enlargement (47) is stopped by the rim (35), a further pulling of the plunger (50) can be stopped when the cutting groove (52) is about flush with the other end of the syringe barrel (10) with the needle (60) being retracted into the syringe barrel (10), and a breaking operation along the cutting groove (52) can break the plunger (50).

6. The disposable safety syringe of claim 5, wherein the number of the projections (14) is at least two.

* * * * *